(12) United States Patent
El-Awa

(10) Patent No.: US 9,340,541 B2
(45) Date of Patent: May 17, 2016

(54) PREPARATION OF NEMATOCIDAL SULFONAMIDES

(71) Applicant: E. I. DU PONT DE NEMOURS AND COMPANY, Wilmington, DE (US)

(72) Inventor: Ahmad El-Awa, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/758,348

(22) PCT Filed: Dec. 31, 2013

(86) PCT No.: PCT/US2013/078398
§ 371 (c)(1),
(2) Date: Jun. 29, 2015

(87) PCT Pub. No.: WO2014/109933
PCT Pub. Date: Jul. 17, 2014

(65) Prior Publication Data
US 2015/0368239 A1    Dec. 24, 2015

Related U.S. Application Data

(60) Provisional application No. 61/751,993, filed on Jan. 14, 2013.

(51) Int. Cl.
| C07D 401/02 | (2006.01) |
| C07D 401/10 | (2006.01) |
| A61K 31/437 | (2006.01) |
| A61K 31/4353 | (2006.01) |
| C07D 471/04 | (2006.01) |

(52) U.S. Cl.
CPC .................................. C07D 471/04 (2013.01)

(58) Field of Classification Search
CPC .. C07D 401/02; C07D 401/10; A61K 31/437; A61K 31/4353
USPC .......................................... 546/121; 514/300
See application file for complete search history.

(56) References Cited

FOREIGN PATENT DOCUMENTS

WO    2010129500    * 11/2010

* cited by examiner

*Primary Examiner* — Niloofar Rahmani
(74) *Attorney, Agent, or Firm* — Roman Kucharczyk

(57) ABSTRACT

Disclosed is a method for preparing a compound of Formula 1 by coupling of intermediates of Formula 2 and Formula 3 in the presence of an aluminum reagent of Formula 4

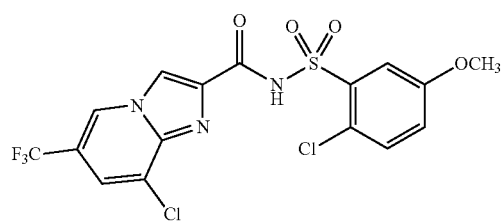

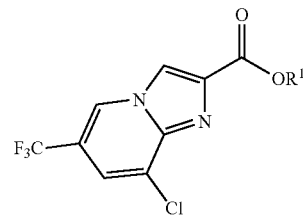

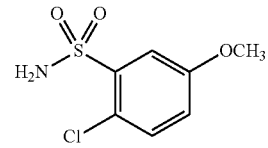

wherein $R^1$, $R^{2a}$, $R^{2b}$ and $R^{2c}$ are defined in the disclosure.

15 Claims, 1 Drawing Sheet

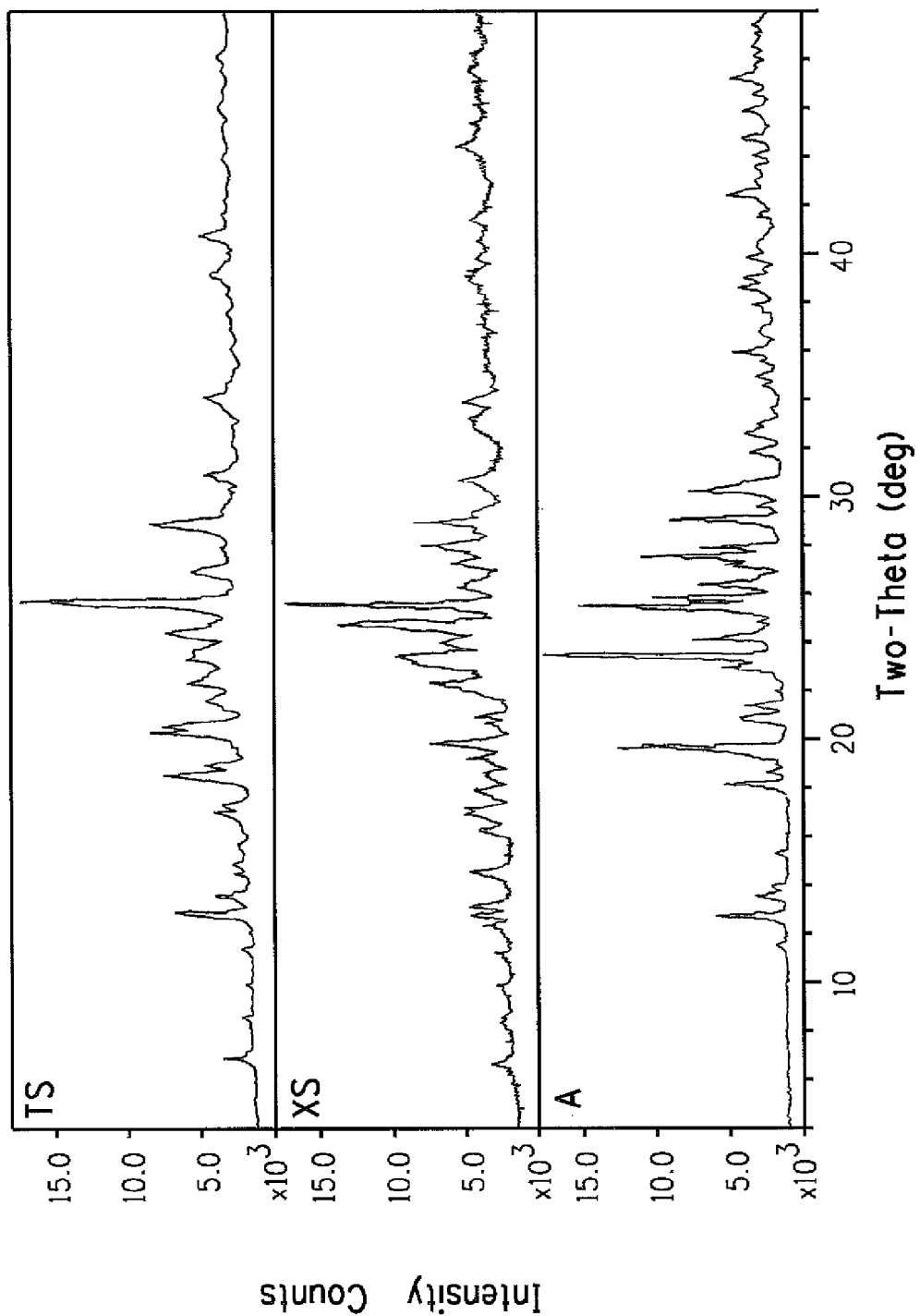

PREPARATION OF NEMATOCIDAL SULFONAMIDES

This invention relates to a novel method for preparing 8-chloro-N-[(2-chloro-5-methoxyphenyl)sulfonyl]-6-(trifluoromethyl)-imidazo[1,2-a]pyridine-2-carboxamide.

BACKGROUND OF THE INVENTION

Preparation of 8-chloro-N-[(2-chloro-5-methoxyphenyl)sulfonyl]-6-(trifluoromethyl)-imidazo[1,2-a]pyridine-2-carboxamide and its use as a nematocide is described in PCT Patent Publication WO 2010/129500. However, the need continues for new or improved methods suitable for rapidly and economically providing 8-chloro-N-[(2-chloro-5-methoxyphenyl)sulfonyl]-6-(trifluoromethyl)-imidazo[1,2-a]pyridine-2-carboxamide.

SUMMARY OF THE INVENTION

The present invention provides a method for preparing a compound of Formula 1

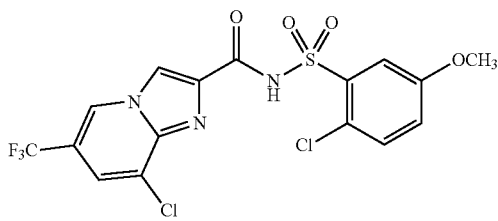

1 comprising (A) contacting a compound of Formula 2

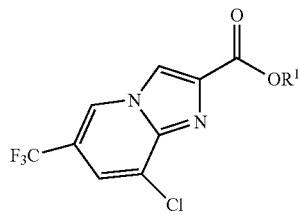

2 wherein
$R^1$ is $C_1$-$C_4$ alkyl
with a compound of Formula 3

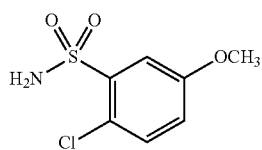

3 and at least one aluminum reagent of Formula 4

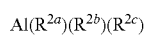

4 wherein
$R^{2a}$, $R^{2b}$ and $R^{2c}$ are each independently H, Cl or $C_1$-$C_4$ alkyl in the presence of an inert solvent to form a first reaction product,
(B) contacting the first reaction product with an $C_1$-$C_4$ alkanol to form a second reaction product
and (C) contacting the second reaction product with water and a protic acid to give the compound of Formula 1.

BRIEF DESCRIPTION OF THE DRAWINGS

FIG. 1 shows Cu(Kα1)-powder X-ray diffraction patterns of polymorph Forms TS, XS and A of Compound 1 showing absolute X-ray intensity in counts graphed against 2θ reflection positions in degrees.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such phrase would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "ambient temperature" or "room temperature" as used in this disclosure refers to a temperature between about 18° C. and about 28° C.

The term "polymorph" refers to a particular crystal form (i.e. structure of crystal lattice) of a chemical compound that can exist in more than one crystal form in the solid state.

In the above recitations, the term "alkyl", includes straight-chain or branched alkyl, such as, methyl, ethyl, n-propyl, i-propyl, or the different butyl isomers. Haloalkanes are alkanes partially or fully substituted with halogen atoms (fluorine, chlorine, bromine or iodine). Examples of haloalkanes include $CH_2Cl_2$, $ClCH_2CH_2Cl$ and $CCl_3CH_3$.

Halogenated benzenes are benzenes partially or fully substituted with halogen atoms (fluorine, chlorine, bromine or iodine). Examples of halogenated benzenes include Chlorobenzene, 1,2-dichlorobenzene and bromo-benzene. $C_7$-$C_{10}$ aromatic hydrocarbons are compounds containing one benzene ring which is substituted with alkyl groups. Examples of $C_7$-$C_{10}$ aromatic hydrocarbons are toluene, xylenes, ethyl benzene and cumene (iso-propylbenzene).

Embodiments of the present invention include:

Embodiment P. A method for preparing the compound of Formula 1

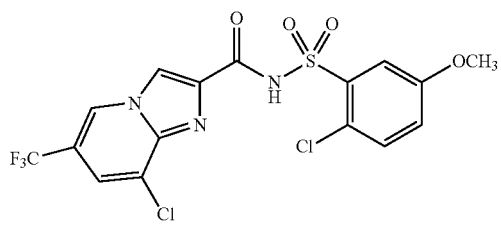

comprising (A) contacting a compound of Formula 2

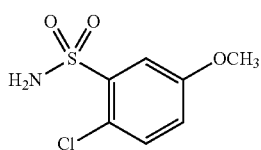

wherein $R^1$ is $C_1$-$C_4$ alkyl with a compound of Formula 3

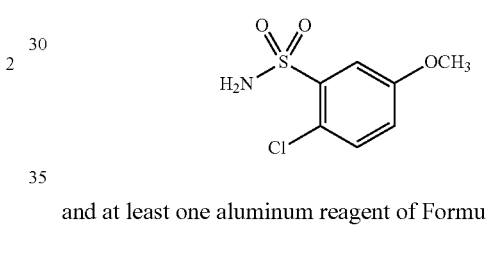

and at least one aluminum reagent of Formula 4p $$Al(R^2)_3 \quad 4p$$

wherein each $R^2$ is independently H, Cl, $CH_3$, $CH_2CH_3$, or $CH_2CH(CH_3)_2$ in the presence of an inert solvent to form a first reaction product, (B) contacting the first reaction product with an $C_1$-$C_4$ alkanol to form a second reaction product and (C) contacting the second reaction product with water and a protic acid to give the compound of Formula 1.

Embodiment 1. The method of Embodiment P or the method described in the Summary of the Invention for preparing the compound of Formula 1

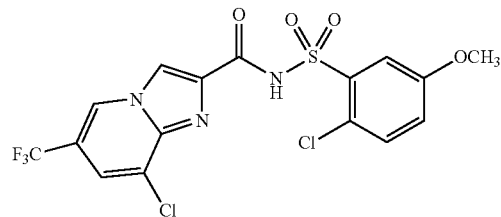

comprising (A) contacting a compound of Formula 2

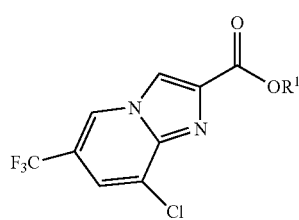

wherein $R^1$ is $C_1$-$C_4$ alkyl with a compound of Formula 3

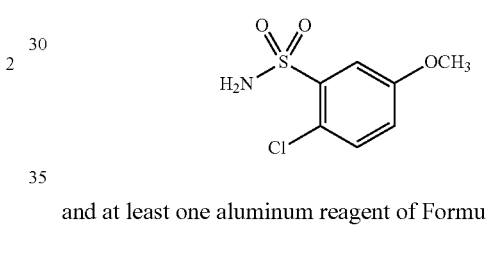

and at least one aluminum reagent of Formula 4

$$Al(R^{2a})(R^{2b})(R^{2c}) \quad 4$$

wherein $R^{2a}$, $R^{2b}$ and $R^{2c}$ are each independently H, Cl or $C_1$-$C_4$ alkyl in the presence of an inert solvent to form a first reaction product, (B) contacting the first reaction product with an $C_1$-$C_4$ alkanol to form a second reaction product and (C) contacting the second reaction product with water and a protic acid to give the compound of Formula 1.

Embodiment 2. The method of Embodiment 1 wherein $R^1$ is $CH_3$, $CH_2CH_3$, $CH_2CH_2CH_3$, $CH(CH_3)_2$, $CH_2CH_2CH_2CH_3$, $CH_2CH(CH_3)_2$ or $CH_2(CH_3)CH_2CH_3$.

Embodiment 3. The method of Embodiment 2 wherein $R^1$ is $CH_3$ or $CH_2CH_3$.

Embodiment 4. The method of Embodiment 3 wherein $R^1$ is $CH_2CH_3$.

Embodiment 5. The method of any one of Embodiments 1 through 4 wherein $R^{2a}$, $R^{2b}$ and $R^{2c}$ are each independently H, Cl, $CH_3$, $CH_2CH_3$ or $CH_2CH(CH_3)_2$.

Embodiment 5p. The method of any one of Embodiments 1 through 4 wherein each $R^2$ is independently Cl, $CH_3$ or $CH_2CH_3$.

Embodiment 6. The method of Embodiment 5p wherein each $R^2$ is independently Cl or $CH_2CH_3$.

Embodiment 7. The method of any one of Embodiments 1 through 6 wherein the at least one aluminum reagent of Formula 4 comprises one or more compounds selected from the group consisting of $ClAl(CH_2CH_3)_2$, $Cl_2Al(CH_2CH_3)$, $Al(CH_2CH_3)_3$, $Al(CH_3)_3$, $Al[CH_2CH(CH_3)_2]_3$ and $HAl[CH_2CH(CH_3)_2]_2$.

Embodiment 8. The method of Embodiment 7 wherein the at least one aluminum reagent of Formula 4 comprises one or more compounds selected from the group consisting of $ClAl(CH_2CH_3)_2$, $Cl_2Al(CH_2CH_3)$ and $Al(CH_2CH_3)_3$.

Embodiment 9. The method of Embodiment 8 wherein the at least one aluminum reagent of Formula 4 comprises $ClAl(CH_2CH_3)_2$.

Embodiment 10. The method of any one of Embodiments 1 through 9 wherein the inert solvent comprises one or more solvents selected from the group consisting of $C_1$-$C_6$ haloalkanes, halogenated benzenes and $C_7$-$C_{10}$ aromatic hydrocarbons.

Embodiment 11. The method of Embodiment 10 wherein the inert solvent comprises one or more solvents selected from the group consisting of toluene, xylenes, ethylbenzene, cumene, 1,2-dichloroethane, dichloromethane, 1,1,1-trichloroethane, chlorobenzene, 1,2-dichlorobenzene and n-chlorobutane.

Embodiment 12. The method of Embodiment 11 wherein the inert solvent comprises toluene.

Embodiment 12a. The method of Embodiment 11 wherein the inert solvent comprises n-chlorobutane.

Embodiment 12b. The method of Embodiment 11 wherein the inert solvent comprises one or more solvents selected from the group consisting of 1,2-dichloroethane, dichloromethane and n-chlorobutane.

Embodiment 12c. The method of Embodiment 12b wherein the inert solvent comprises one or more solvents selected from the group consisting of 1,2-dichloroethane and dichloromethane.

Embodiment 12d. The method of Embodiment 12c wherein the inert solvent comprises 1,2-dichloroethane.

Embodiment 12e. The method of Embodiment 12c wherein the inert solvent comprises dichloromethane.

Embodiment 13. The method of any one of Embodiments 1 through 12e wherein in step (A) the temperature is in the range of 20 to 150° C.

Embodiment 14. The method of Embodiment 13 wherein in step (A) the temperature is in the range of 50 to 100° C.

Embodiment 15. The method of Embodiment 14 wherein in step (A) the temperature is in the range of 60 to 80° C.

Embodiment 16. The method of any one of Embodiments 1 through 15 wherein in step (A) the temperature is in the range of 50 to 100° C., the inert solvent comprises dichloromethane, and the pressure above the inert solvent is in the range of 100 to 700 kPa.

Embodiment 16a. The method of any one of Embodiments 1 through 16 wherein in step (A), the compound of Formula 2 and the compound of Formula 3 are combined in the presence of an inert solvent and then the aluminum reagent of Formula 4 is added.

Embodiment 17. The method of any one of Embodiments 1 through 16a wherein the molar ratio of the compound of Formula 2 to the compound of Formula 3 is in the range of 1.1:1.0 to 1.0:1.1.

Embodiment 18. The method Embodiment 17 wherein the molar ratio of the compound of Formula 2 to the compound of Formula 3 is 1.0:1.0.

Embodiment 19. The method of any one of Embodiments 1 through 18 wherein the molar ratio of the compound of Formula 2 to the aluminum reagent is in the range of 1.0:1.0 to 1.0:1.5.

Embodiment 20. The method of Embodiment 19 wherein the molar ratio of the compound of Formula 2 to the aluminum reagent is 1.0:1.1.

Embodiment 21. The method of any one of Embodiments 1 through 20 wherein in step (B) the $C_1$-$C_4$ alkanol comprises one or more alkanols selected from the group consisting of methanol, ethanol, n-propanol, iso-propanol, n-butanol, iso-butanol and sec-butanol.

Embodiment 22. The method of Embodiment 21 wherein in step (B) the $C_1$-$C_4$ alkanol comprises one or more alkanols selected from the group consisting of methanol, ethanol, n-propanol or iso-propanol.

Embodiment 23. The method of Embodiment 22 wherein in step (B) the $C_1$-$C_4$ alkanol comprises iso-propanol.

Embodiment 24. The method of any one of Embodiments 1 through 23 wherein in step (B) the molar ratio of the $C_1$-$C_4$ alkanol to the compound of Formula 2 is in the range of 2.5:1.0 to 1.8:1.0.

Embodiment 25. The method of Embodiment 24 wherein in step (B) the molar ratio of the $C_1$-$C_4$ alkanol to the compound of Formula 2 is 2.0:1.0.

Embodiment 26. The method of any one of Embodiments 1 through 25 wherein in step (B) the temperature is in the range of 20 to 80° C.

Embodiment 27. The method of Embodiment 26 wherein in step (B) the temperature is in the range of 50 to 80° C.

Embodiment 28. The method of any one of Embodiments 1 through 27 wherein in step (C) the protic acid comprises one or more protic acids selected from the group consisting of acetic acid, hydrochloric acid, citric acid, formic acid and sulfuric acid.

Embodiment 29. The method of Embodiment 28 wherein in step (C) the protic acid comprises acetic acid.

Embodiment 30. The method of any one of Embodiments 1 through 29 wherein in step (C) the temperature is in the range of 20 to 30° C.

Embodiment 31. The method of any one of Embodiments 1 through 30 wherein in step (C) the molar ratio of the protic acid to the compound of Formula 2 is in the range of 3.0:1.0 to 2.0:1.0.

Embodiment 32. The method of Embodiment 31 wherein in step (C) the molar ratio of the protic acid to the compound of Formula 2 is 2.5:1.0.

Embodiments of this invention, including Embodiments P and 1-32 above as well as any other embodiments described herein, can be combined in any manner, and the descriptions of variables in the embodiments pertain not only to the aforedescribed method for preparing the compound of Formula 1, but also to the starting compounds and intermediate compounds useful for preparing the compound of Formula 1 by this method. In the Embodiments of this invention, references to Formula 4 are considered to also refer to Formula 4p.

In the following Scheme 1 the definition of $R^1$ and $R^2$ in the compounds of Formulae 2 and 4 are as defined above in the Summary of the Invention and description of Embodiments unless otherwise indicated.

In the method of the invention, a compound of Formula 2 is reacted with a compound of Formula 3 in the presence of an aluminum reagent of Formula 4 to form the compound of Formula 1 after treatment with an alcohol and aqueous acid. Step (A) of the method of the invention involves coupling of a compound of Formula 2 with a compound of Formula 3 in the presence of at least one aluminum reagent of Formula 4 to form a first reaction product. In step (B), the first reaction product, i.e. $P^A$, is treated with an $C_1$-$C_4$ alkanol to form a second reaction product. In step (C), the second reaction product, i.e. $P^B$, is treated with a protic acid in water to give the compound of Formula 1 as shown in Scheme 1.

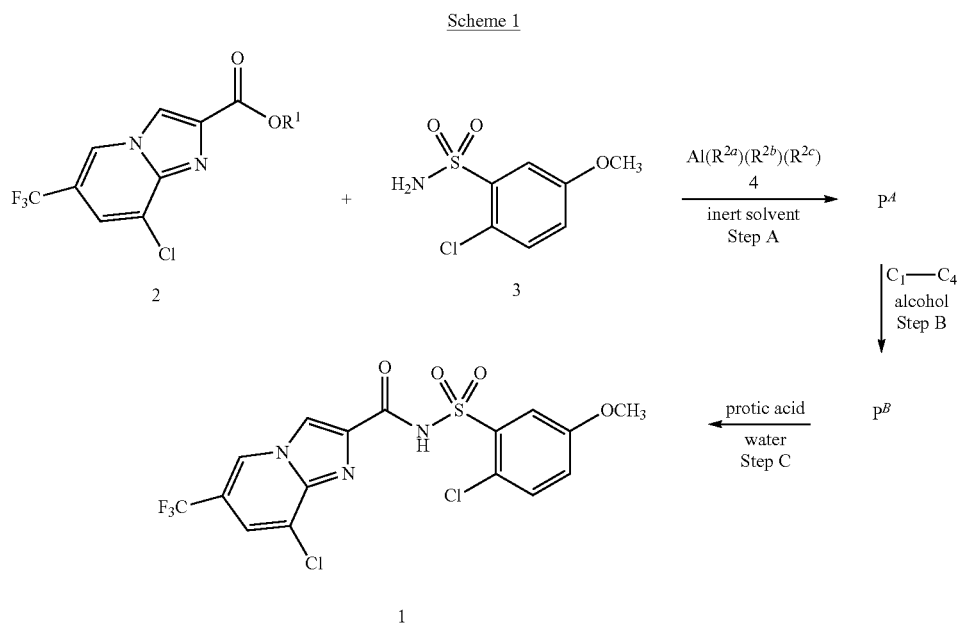

Scheme 1

The first reaction product $P^A$ and the second reaction product $P^B$ are usually not isolated but believed to be aluminum complexes. The reaction mixture containing $P^A$ is used directly in Step (B) and the reaction mixture containing $P^B$ is used directly in Step (C).

Examples of aluminum reagents of Compound 4 which can be used in step (A) of the coupling of compounds of Formula 2 with compounds of Formula 3 include but are not limited to $ClAl(CH_2CH_3)_2$, $Cl_2Al(CH_2CH_3)$, $Al(CH_2CH_3)_3$, $Al(CH_3)_3$, $Al[CH_2CH(CH_3)_2]_3$ and $HAl[CH_2CH(CH_3)_2]_2$. A particularly useful aluminum reagent for the coupling of Step (A) is $ClAl(CH_2CH_3)_2$, i.e. diethylaluminum chloride.

Aluminum reagents are sensitive to the presence of both air and water in the process of Scheme 1. Many, such as diethylaluminum chloride, are pyrophoric, and spontaneously ignite in the presence of air and water. Therefore the process is preferentially carried out in a substantially oxygen and water free solvent. Standard techniques can be used to obtain oxygen-free solvents including, for example, refluxing or distilling the solvents in an inert atmosphere such as nitrogen or argon, or sparging the solvents with an inert gas such as nitrogen or argon. Standard drying agents such as molecular sieves, potassium carbonate and magnesium sulfate may be used.

The coupling of compounds of Formula 2 with compounds of Formula 3 in step (A) can be accomplished in inert solvents such as $C_1$-$C_6$ haloalkanes, halogenated benzenes and $C_7$-$C_{10}$ aromatic hydrocarbons. Examples of these types of solvents include but are not limited to toluene, xylenes, ethylbenzene, cumene, 1,2-dichloroethane, dichloromethane, 1,1,1-trichloroethane, chlorobenzene, 1,2-dichlorobenzene and n-chlorobutane. Particularly useful solvents for this coupling are toluene, n-chlorobutane, 1,2-dichloroethane and dichloromethane. Haloalkane solvents (e.g. n-chlorobutane, 1,2-dichloroethane and dichloromethane) are especially useful because the Compound of Formula 1 can be isolated in unsolvated form (polymorph Form A) from them.

The coupling of compounds of Formula 2 with compounds of Formula 3 in step (A) can be run under a broad range of temperatures, i.e. temperatures in the range of 20 to 150° C. Temperatures in the range of 50 to 100° C. are particularly useful. Temperatures in the range of 60 to 80° C. are especially useful.

The reaction in dichloromethane (boiling point 40° C.) at atmospheric pressure, takes about 24 hours to reach completion. In order to reduce the reaction time in dichloromethane, the reaction can be run at reaction temperatures (50 to 100° C.) above the boiling point under a moderate pressure of 100 to 700 kPa (about 15 to 100 psi). Reaction times at the higher temperatures are much shorter (1 to 3 hours). Standard engineering techniques and equipment known in the art of process chemistry can be used to maintain a reaction vessel under temperatures and pressures in this range.

In step (A) the molar ratio of the compound of Formula 2 to the compound of Formula 3 is in the range of 1.1:1.0 to 1.0:1.1. An especially useful molar ratio of the compound of Formula 2 to the compound of Formula 3 is 1.0:1.0.

In step (A) the molar ratio of the compound of Formula 2 to the aluminum reagent of Formula 4 is in the range of 1.0:1.0 to 1.0:1.5. An especially useful molar ratio of the compound of Formula 2 to the compound of Formula 3 is 1.0:1.1.

Step (A) of Scheme 1 can be carried out using standard engineering practice. Preferably the reagents are charged to the reaction vessel in an oxygen-free environment. Standard techniques for obtaining an oxygen-free environment can be used, including, for example, evacuating the reaction vessel and re-pressurizing to atmospheric pressure with an inert gas. This method can be repeated two or more times to further reduce the oxygen present in the reaction vessel.

The reagents of Formulae 2, 3 and 4 in step (A) of the invention can be combined in a variety of orders. A particularly useful method is to combine the compound of Formula 2 and the compound of Formula 3 in the presence of an inert solvent followed by addition of the aluminum reagent of Formula 4. The rate of addition of the aluminum reagent should be slow enough to maintain the temperature in the range of 60 to 80° C. After the addition of the aluminum reagent 4 the reaction mixture is typically a thick slurry requiring efficient stirring.

In step (B), the first reaction product, i.e. $P^A$, is treated with an $C_1$-$C_4$ alkanol such as methanol, ethanol, n-propanol, iso-propanol, n-butanol, iso-butanol or sec-butanol. Particularly useful solvents are methanol, ethanol, n-propanol or iso-propanol. An especially useful alkanol is iso-propanol.

In step (B) the molar ratio of the $C_1$-$C_4$ alkanol to the compound of Formula 2 is in the range of 2.5:1.0 to 1.8:1.0. A particularly useful molar ratio of the $C_1$-$C_4$ alkanol to the compound of Formula 2 is 2.0:1.0.

Treatment of the first reaction product $P^A$ in step (B) with a $C_1$-$C_4$ alkanol can be carried out under a broad range of temperatures, i.e. temperatures in the range of 20 to 80° C. Temperatures in the range of 50 to 80° C. are particularly useful.

In step (C), the second reaction product, i.e. $P^B$, is treated with a protic acid in the presence of water. Examples of protic acids include, but are not limited to acetic acid, hydrochloric acid, citric acid, formic acid and sulfuric acid. A particularly useful acid is acetic acid.

In step (C) the molar ratio of the protic acid to the compound of Formula 2 is in the range of 3.0:1.0 to 2.0:1.0. A particularly useful molar ratio of the protic acid to the compound of Formula 2 is 2.5:1.0.

Treatment of the second reaction product $P^B$ in step (C) with a protic acid can be carried out in the temperature range of 20 to 30° C.

Reaction progress can be monitored by conventional methods such as HPLC and $^1$H NMR analyses of aliquots.

The compounds of Formula 2 and Formula 3 used in step (A) of the invention are prepared as described in PCT Patent Publication WO 2010/129500. Many Aluminum reagents of Formula 4 are commercially available.

The compound of Formula 1 can optionally be isolated by standard techniques known in the art, including filtration, extraction, evaporation, and crystallization. As the compound of Formula 1 is a solid at ambient temperature, it is most easily isolated by filtration, optionally followed by washing with water and/or an organic solvent (xylenes, toluene, n-chlorobutane). Additional product can be isolated by concentrating the filtrate under reduced pressure, slurrying the resulting residue in an organic solvent, filtering and optionally washing with water and/or an organic solvent (xylenes, toluene, n-chlorobutane). The solid product can be further purified by recrystallization from an appropriate organic solvent.

The solid state of Compound 1 is preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g. lattice type) in the solid state. Crystalline forms of Compound 1 in this invention relate to single polymorphs (i.e. single crystalline form). Polymorphs can differ in such chemical, physical and biological properties as crystal shape, density, hardness, color, chemical stability, melting point, hygroscopicity, suspensibility, solubility, dissolution rate and biological availability. One skilled in the art will appreciate that a polymorph of Compound 1 can exhibit beneficial effects (e.g., suitability for preparation of useful formulations, stability, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and efficacy of nematode control.

One crystalline polymorph form of Compound 1, designated as polymorph Form TS, is a 1:1 (molar ratio) toluene solvate. Polymorph Form TS can be characterized by X-ray powder diffraction.

The powder X-ray diffraction pattern of polymorph Form TS of Compound 1 is shown in FIG. 1. The corresponding 2θ values are tabulated in Table 1 of Characterization Example 1. Polymorph Form TS of Compound 1 can be identified by a room-temperature powder Cu(Kα1) X-ray diffraction pattern having at least the 2θ reflection positions (in degrees)

| 2θ | 2θ |
|---|---|
| 28.913 | 22.429 |
| 26.942 | 20.325 |
| 25.672 | 19.053 |
| 24.451 | 18.603 |
| 23.316 | 12.871 |

Polymorph Form TS can be prepared directly during the preparation of Compound 1 from its starting materials in the presence of toluene solvent as described in Preparation Example 1.

A second crystalline polymorph form of Compound 1 is designated as polymorph Form A. This solid form is unsolvated. Polymorph Form A can be characterized by its powder X-ray diffraction pattern.

The powder X-ray diffraction pattern of polymorph Form A of Compound 1 is shown in FIG. 1. The corresponding 2θ values are tabulated in Table 2 of Characterization Example 2. Polymorph Form A of Compound 1 can be identified by a room-temperature powder Cu(Kα1) X-ray diffraction pattern having at least the 2θ reflection positions (in degrees)

| 2θ | 2θ |
|---|---|
| 30.367 | 25.973 |
| 29.131 | 25.604 |
| 27.995 | 24.285 |
| 27.611 | 23.582 |
| 26.49 | 19.789 |

Polymorph form A can be prepared from Polymorph Form TS as described in Preparation Example 2.

Polymorph Form A can also be prepared directly during the preparation of Compound 1 from its starting materials in the presence of n-chlorobutane solvent as described in Preparation Example 3.

A third crystalline polymorph form of Compound 1 designated as polymorph Form XS is a xylenes solvate. Polymorph Form XS can be characterized by its powder X-ray diffraction pattern.

The powder X-ray diffraction pattern of polymorph Form XS of Compound 1 is shown in FIG. 1. The corresponding 2θ values are tabulated in Table 3 of Characterization Example 3. Polymorph Form XS of Compound 1 can be identified by a room-temperature powder Cu(Kα1) X-ray diffraction pattern having at least the 2θ reflection positions (in degrees)

| 2θ | 2θ |
|---|---|
| 30.767 | 24.836 |
| 28.964 | 24.100 |
| 28.045 | 23.499 |
| 26.324 | 22.397 |
| 25.621 | 19.906 |

Polymorph Form XS can be prepared directly during the preparation of Compound 1 from its starting materials in the presence of xylenes solvent as described in Preparation Example 4.

Without further elaboration, it is believed that one skilled in the art using the preceding description can utilize the present invention to its fullest extent. The following Examples are, therefore, to be construed as merely illustrative, and not limiting of the disclosure in any way whatsoever. Abbreviations used in the examples are as follows: rpm is revolutions per minute, pXRD is powder X-ray diffraction, wt % is percent by weight measured by HPLC (using a calibration standard), a % is percent by area measured by HPLC at a wavelength of 230 nm.

Analytical methods used in the preparation examples are described below or in the Characterization Examples.

Powder X-ray Diffraction (p-XRD)

Powder X-ray diffraction was used to identify the crystalline phases of various samples of Compound 1. Data were obtained with a Philips X'PERT automated powder diffractometer, Model 3040. The radiation produced by a copper anode X-ray source includes Cu—K(alpha1), Cu—K(alpha2) and Cu—K(beta). The diffractometer was equipped with a nickel filter that removes the Cu—K(beta) radiation leaving Cu—K(alpha1) and Cu—K(alpha2) in the raw data. The peaks originating from Cu—K(alpha2) are removed during the find peaks routine in the Jade Software (MDI/Jade software version 9.1) leaving the listed maxima from Cu—K(alpha1). The wavelength for Cu—K(alpha1) or Cu(Kα1) radiation listed in International Tables for X-ray Crystallography is 0.154056 nm.

High Performance Liquid Chromatography (HPLC)

HPLC analyses were performed using a Hewlett Packard 1100 series HPLC system with DAD/UV detector and reverse-phase column (Agilent Eclipse XDB-C8 (4.6×150) mm, 5 μm, Part. No. 993967-906). Flow rate was 1.0 mL/min, run time 25 min, injection volume 3.0 μL, and the column temperature was 40° C. Mobile phase A was 0.075% orthophosphoric acid (aq) and mobile phase B was acetonitrile (HPLC grade). For wt % determination the concentration of the test sample was calibrated against a standard sample, and a % purity reported from the sample chromatogram. Peaks appearing in the blank sample were not integrated, all other peaks were integrated and a % purity reported from the sample chromatogram. For wt % determination the concentration of test sample was calibrated against the standard sample.

Proton—Nuclear Magnetic Resonance ($^1$H NMR)

Proton-NMR analysis was performed on a Bruker Advance 300/400 instrument. The operational frequency was 400 MHz, spectral frequency range 0-16 ppm, delay time 2 seconds, pulse width of 12 μs, minimum number of scans was 8. Samples were prepared by weighing about 0.01 g of samples or reference standards, adding 0.6 mL of DMSO-$d_6$ to dissolve the contents and transferring into NMR tubes. Deuterated DMSO (DMSO-$d_6$) was from Cambridge Isotope Laboratory. $^1$H NMR spectra are reported in ppm downfield from tetramethylsilane; "s" means singlet, "d" means doublet and "dd" means doublet of doublets.

PREPARATION EXAMPLE 1

Preparation of Toluene Solvate Form of 8-chloro-N-[(2-chloro-5-methoxyphenyl)sulfonyl]-6-(trifluoromethyl)-imidazo[1,2-a]pyridine-2-carboxamide (Form TS)

A stirred slurry of 8-chloro-6-(trifluoromethyl)imidazo[1,2,a]pyridine-2-carboxylic acid ethyl ester (see PCT Patent Publication WO 2010/129500 for preparation) (10 g, 33.7 mmol based on HPLC wt %=98.9%) and 2-chloro-5-methoxybenzenesulfonamide (see PCT Patent Publication WO 2010/129500 for preparation) (8 g, 35.9 mmol, 1.05 equiv) in toluene (70 mL) at 23° C. under nitrogen was heated to 55° C. over a period of 60 min. To this slurry under nitrogen was added 1M diethyl aluminum chloride in toluene (34 mL, 33.7 mmol, 1 equiv) over approximately 10 minutes. The addition of diethylaluminum chloride was accompanied by ca. 10° C. temperature rise and moderate foaming. After complete addition of diethylaluminum chloride the temperature of the reaction mixture was adjusted to 75° C. over a period of 30 min. The reaction mixture was held with efficient stirring for 4 h at 73-75° C. during which it became a very thick slurry. After about 4 h, HPLC analysis indicated <1 area % of 8-chloro-6-(trifluoromethyl)imidazo[1,2,a]pyridine-2-carboxylic acid ethyl ester remaining. Iso-propanol (5.2 mL, 68.3 mmol, 2 equiv) was added and the mixture was subsequently cooled to 20-25° C. Aqueous 10% acetic acid (47 mL, 85.4 mmol, 2.5 equiv) was then added over a period of 1 h at 20-35° C. The reaction was held for an additional 1 h at 25° C. and then filtered, washed successively with water (80 ml) and toluene (20 mL), and suction-dried for 5 h. The solid product was further dried in a vacuum oven at 80° C. for 90 h to give the title compound (13.7 g) as an off-white solid with purity=98.6 a % (by HPLC); assay=97.9 wt % (by HPLC).

$^1$H-NMR was consistent with Compound 1 [(DMSO-$d_6$) δ 3.86 (s, 3H), 7.30 (d, 1H), 7.57 (dd, 1H), 7.64 (d, 1H), 7.96 (d, 1H), 8.84 (s, 1H), 9.34 (d, 1H)] containing toluene. The molar ratio of toluene and Compound 1 is 1 indicating a 1:1 toluene solvate. The polymorph Form TS was characterized by its powder X-ray diffraction pattern (See Characterization Example 1).

PREPARATION EXAMPLE 2

Conversion of the Toluene Solvate Form of Compound 1 to Form A

To a 500 mL three-neck round-bottom flask equipped with overhead stirrer, oil bath, a Dean-Stark apparatus and temperature probe was charged 25 g of Compound 1 (toluene content=17.3 wt %) and water (75 mL) at 25° C. The resultant reaction mass was heated to 95° C. (reaction mass temperature) and maintained at 95-96° C. over a period of 5 h while stirring at about 850 rpm. The water collected from the Dean-Stark apparatus was recycled to maintain about constant reaction volume while toluene was removed from the reaction mixture. After about 3 h no further distillation of toluene was observed. A slurry sample was taken from the reaction mass under agitation. The toluene and ethyl acetate content of the slurry was determined by GC analysis as 56 ppm and 17 ppm, respectively. About 10 mL of the sample was taken from the reaction mixture, cooled to 25° C., filtered and vacuum dried on a Büchner funnel for 15 min. The wet cake showed about 429 ppm of toluene and 36 ppm of ethyl acetate. The wet cake was dried in a vacuum oven at 55° C. (8-15 kPa absolute pressure) for about 1 hour to afford the title compound.

$^1$H-NMR was consistent with Compound 1 [(DMSO-d$_6$) δ 3.86 (s, 3H), 7.30 (d, 1H), 7.57 (dd, 1H), 7.64 (d, 1H), 7.96 (d, 1H), 8.84 (s, 1H), 9.34 (d, 1H)] in unsolvated form. Polymorph Form A was characterized by its powder X-ray diffraction pattern (See Characterization Example 2).

Since the portion of the sample from the reaction mass indicated the conversion to Form A, the entire reaction mass was filtered, dried in a vacuum oven (8-15 kPa absolute pressure) at 55° C. for 1 h to afford additional title compound.

PREPARATION EXAMPLE 3

Direct Preparation of Polymorph Form A of 8-chloro-N-[(2-chloro-5-methoxyphenyl)-sulfonyl]-6-(trifluoromethyl)-imidazo[1,2-a]pyridine-2-carboxamide A stirred slurry of 8-chloro-6-(trifluoromethyl)imidazo[1,2,a]pyridine-2-carboxylic acid ethyl ester (3.0 g, 10.3 mmol) and 2-chloro-5-methoxybenzenesulfonamide (2.39 g, 10.8 mmol, 1.05 equiv) in n-chlorobutane (45 mL) was heated to 50° C. under nitrogen. To this slurry was added neat diethylaluminum chloride (1.40 mL, 11.3 mmol). After complete addition of diethylaluminum chloride the temperature of the reaction mixture was adjusted to 65-70° C. and was held at this temperature for 4.5 h. An additional portion of n-chlorobutane (12 mL) was added and heating at 70° C. was continued for an additional 1.5 h. Iso-propanol (1.6 mL, 20.5 mmol, 2 equiv) was added at 70° C. and the resulting mixture stirred for 5 min. Aqueous 10% acetic acid (15 mL, 25.6 mmol, 2.5 equiv) was then added over a period of 10 min at 60-65° C. The reaction was allowed to cool to room temperature and then stirred overnight. The resulting solid was filtered, washed with water (12 mL) followed by n-chlorobutane (12 mL), and suction-dried. The solid product was further dried in a vacuum oven at 50-60° C. to give the title compound (4.09 g, 85.2%). Powder X-ray diffraction data conformed with Form A of Compound 1 as in Characterization Example 2.

PREPARATION EXAMPLE 4

Preparation of Xylene Solvate Form of 8-chloro-N-[(2-chloro-5-methoxyphenyl)sulfonyl]-6-(trifluoromethyl)-imidazo[1,2-a]pyridine-2-carboxamide (Form XS)

A stirred slurry of 8-chloro-6-(trifluoromethyl)imidazo[1,2,a]pyridine-2-carboxylic acid ethyl ester (5.0 g, 17.1 mmol) and 2-chloro-5-methoxybenzenesulfonamide (3.98 g, 17.9 mmol) in xylenes (60 mL) at 23° C. under nitrogen was heated to 60° C. To this slurry was added neat diethyl aluminum chloride (2.4 mL, 18.8 mmol) over approximately 5 minutes. The addition of diethylaluminum chloride was accompanied by ca. 15° C. temperature rise and moderate foaming. Heating was continued for 1.5 h. The reaction mixture was then diluted with xylenes (5 mL) and then heated at 60° C. for an additional 2 h. The reaction mixture was cooled to 53° C. Iso-propanol (2.6 mL, 34.17 mmol) was added and the reaction mixture subsequently cooled to 20-25° C. Hydrochloric acid (2N, 22 mL, 42.7 mmol) was then added over a period of 30 min. The reaction was then filtered, washed successively with water (20 mL) and xylenes (10 mL) to yield a solid. A portion of the solid product (1.5 g) was slurried in a mixture of acetic acid (0.75 mL) and water (15 mL), heated to 75° C. with efficient stirring, and held at this temperature for 4 h. The reaction mixture was filtered hot and the filtered solid washed with water (6 mL) and the solid dried in a vacuum oven at 45° C. overnight to give the title compound (0.91 g) as an off-white solid.

$^1$H-NMR was consistent with Compound 1 [(DMSO-d$_6$) δ 3.86 (s, 3H), 7.30 (d, 1H), 7.57 (dd, 1H), 7.64 (d, 1H), 7.96 (d, 1H), 8.84 (s, 1H), 9.34 (d, 1H)] containing xylenes. The polymorph Form XS was characterized by its powder X-ray diffraction pattern (See Characterization Example 3).

PREPARATION EXAMPLE 5

Direct Preparation of Polymorph Form A of 8-chloro-N-[(2-chloro-5-methoxyphenyl)-sulfonyl]-6-(trifluoromethyl)-imidazo[1,2-a]pyridine-2-carboxamide To a stirred slurry of 8-chloro-6-(trifluoromethyl)imidazo[1,2,a]pyridine-2-carboxylic acid ethyl ester (see PCT Patent Publication WO 2010/129500 for preparation) (8 g, 27.3 mmol) and 2-chloro-5-methoxybenzenesulfonamide (see PCT Patent Publication WO 2010/129500 for preparation) (6.4 g, 28.7 mmol, 1.05 equiv) in 1,2-dichloroethane (41 mL) at 22° C. under nitrogen was added diethylaluminum chloride (4 mL, 31.9 mmol, 1.18 equiv) over approximately 5 minutes. The addition of diethylaluminum chloride was accompanied by about 23° C. temperature rise and moderate foaming. After complete addition of diethylaluminum chloride the temperature of the reaction mixture was adjusted to 75° C. The reaction mixture was held with efficient stirring for about 1.5 h at 75° C. during which it became an off-white slurry. After about 1.5 h, HPLC analysis indicated <1 area % of 8-chloro-6-(trifluoromethyl)imidazo[1,2,a]pyridine-2-carboxylic acid ethyl ester remaining. Aqueous 10% acetic acid (41 mL, 68.3 mmol, 2.5 equiv) was then added resulting in some frothing and the reaction mass transformed to a thick slurry and then to a clear biphasic solution. The reaction mass was then cooled down to 45° C. and the two phases separated. The organic phase was then transferred to a jacketed-reactor together with additional 1,2-dichloroethane (20 mL) that was used to dissolve some precipitated solids. The organic phase was heated to distill 1,2-dichloroethane under atmospheric pressure. After collection of about 30 ml of the distillate, acetic acid (17 mL) was added to the jacketed-reactor and distillation continued. When the reactor's temperature reached 102° C., water (64 mL) was added to it and distillation continued. After collection of another 30 mL of distillate, water (about 40 mL) was added to the reactor, the distillation was ended and the batch brought down to room temperature. The batch was then warmed to 75° C. and held stirring for about 5.5 h. The batch was then cooled to room temperature and then filtered. The filter cake was washed with water (20 ml). The solid product was split into two portions, the larger portion was dried in a vacuum oven at 80° C. for 16 hours and the smaller portion was air-dried for 16 hours to give the title compound (9.98 g and 1.48 g respectively) in 89.6% combined yield and with purity=96.7 a % (by HPLC). Both the air-dried and the vacuum-dried product conformed with polymorph Form A.

The polymorph Form A was characterized by its powder X-ray diffraction pattern (See Characterization Example 2).

PREPARATION EXAMPLE 6

Direct Preparation of Polymorph Form A of 8-chloro-N-[(2-chloro-5-methoxyphenyl)-sulfonyl]-6-(trifluoromethyl)-imidazo[1,2-a]pyridine-2-carboxamide To a stirred slurry of 8-chloro-6-(trifluoromethyl)imidazo[1,2-a]pyridine-2-carboxylic acid ethyl ester (see PCT Patent Publication WO 2010/129500 for preparation) (3 g, 10.3 mmol) and 2-chloro-5-methoxybenzenesulfonamide (see PCT Patent Publication WO 2010/129500 for preparation) (2.4 g, 10.8 mmol, 1.05 equiv) in dichloromethane (24 mL) at 17° C. under nitrogen was added diethyl aluminum chloride (1.5 mL, 12.0 mmol, 1.16 equiv) over approximately 1 minute. The addition of diethylaluminum chloride was accompanied by ca. 13° C. temperature rise and gas evolution. After complete addition of diethylaluminum chloride the temperature of the reaction mixture was adjusted to 40° C. and the batch became an off-white slurry. The reaction mixture was held stirring for about 24 h at 40° C. HPLC analysis (after 24 h) indicated 3.6 area % of 8-chloro-6-(trifluoromethyl)imidazo[1,2-a]pyridine-2-carboxylic acid ethyl ester remaining. Iso-propyl alcohol (1.6 mL) and heptane (12 mL) were respectively added to the reaction resulting in formation of a thicker slurry. Aqueous 10% acetic acid (15 mL, 25.6 mmol, 2.5 equiv) was then added resulting in a strong exotherm. The reaction mass was held for about 1.5 h at 20-25° C. and was then filtered and the filter cake was washed with water (12 ml). The solid product was split into two portions, the larger portion was dried in a vacuum oven at 80° C. for 16 hours and the smaller portion was air-dried for 16 hours to give the title compound (2.8 g and 0.95 g respectively) in 86.8% combined yield. The vacuum-dried product conformed with polymorph Form A and the air-dried portion did not. The polymorph Form A was characterized by its powder X-ray diffraction pattern (See Characterization Example 2).

CHARACTERIZATION EXAMPLE 1

X-ray Powder Diffraction Pattern for Compound 1 Polymorph Form TS (BA9507)

Powder X-ray diffraction was used to characterize the toluene solvate polymorph form (Polymorph Form TS) of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu—K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 was used with the International Committee for Diffraction Data database PDF4+2008 for phase identification. Cu—K(alpha1) X-ray diffraction maxima for Form TS of Compound 1 were calculated using the MDI/Jade "Find Peaks" routine and are listed Table 1.

TABLE 1

2θ X-ray Maxima (in degrees) for Polymorph Form TS of Compound 1

| 2θ |
|---|
| 6.889 |
| 8.608 |
| 9.997 |
| 11.433 |
| 12.871 |
| 13.606 |
| 14.508 |
| 14.908 |
| 15.728 |
| 16.481 |
| 16.998 |
| 17.433 |
| 18.603 |
| 19.053 |
| 20.325 |
| 21.643 |
| 22.429 |
| 23.316 |
| 24.451 |
| 25.672 |
| 26.942 |
| 27.945 |
| 28.913 |
| 30.951 |
| 32.222 |
| 32.671 |
| 33.561 |
| 33.994 |
| 34.528 |
| 36.114 |
| 36.906 |
| 37.452 |
| 38.323 |
| 39.057 |
| 40.711 |
| 41.548 |
| 42.015 |
| 43.869 |
| 45.173 |
| 46.092 |
| 47.514 |
| 48.148 |

CHARACTERIZATION EXAMPLE 2

X-ray Powder Diffraction for Compound 1 Polymorph Form A

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu—K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were ground with an agate mortar and pestle as needed and prepared on low background amorphous silica specimen holders as a thin layer of powdered material. MDI/Jade software version 9.1 is used with the International Committee for Diffraction Data database PDF4+2008 for phase identification. Cu—K(alpha1) X-ray diffraction maxima for Form A of Compound 1 were calculated using the MDI/Jade "Find Peaks" routine and are listed Table 2.

TABLE 2

2θ X-ray Maxima (in degrees) for Polymorph Form A of Compound 1

| 2θ |
|---|
| 11.651 |
| 12.854 |
| 13.705 |
| 14.056 |
| 15.426 |
| 18.286 |
| 18.836 |
| 19.789 |
| 21.026 |
| 21.543 |
| 23.097 |
| 23.582 |
| 24.285 |
| 24.584 |
| 24.954 |
| 25.604 |
| 25.973 |
| 26.490 |
| 27.308 |
| 27.611 |
| 27.995 |
| 29.131 |
| 29.764 |
| 30.367 |
| 30.652 |
| 31.905 |
| 32.657 |
| 33.042 |
| 34.629 |
| 35.028 |
| 35.614 |
| 35.982 |
| 36.967 |
| 37.703 |
| 37.956 |
| 38.607 |
| 38.992 |
| 39.875 |
| 40.443 |
| 41.632 |
| 42.451 |
| 42.935 |
| 43.538 |
| 44.089 |
| 44.740 |
| 45.926 |
| 46.644 |
| 47.279 |
| 47.813 |
| 48.167 |
| 48.648 |
| 49.118 |
| 49.502 |

CHARACTERIZATION EXAMPLE 3

X-ray Powder Diffraction for Compound 1 Polymorph Form XS

Powder X-ray diffraction was used to characterize the xylene solvate polymorph form (Polymorph Form XS) of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu—K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 was used with the International Committee for Diffraction Data database PDF4+2008 for phase identification. Cu—K(alpha1) X-ray diffraction maxima for Form XS of Compound 1 were calculated using the MDI/Jade "Find Peaks" routine and are listed Table 1.

TABLE 3

2θ X-ray Maxima (in degrees) for Polymorph Form XS of Compound 1

| 2θ |
|---|
| 6.786 |
| 8.392 |
| 9.911 |
| 11.283 |
| 12.45 |
| 12.903 |
| 13.273 |
| 14.593 |
| 16.394 |
| 17.233 |
| 17.934 |
| 18.719 |
| 19.306 |
| 19.906 |
| 20.707 |
| 21.045 |
| 22.397 |
| 23.499 |
| 24.1 |
| 24.836 |
| 25.621 |
| 26.324 |
| 27.359 |
| 28.045 |
| 28.964 |
| 29.365 |
| 30.767 |
| 31.415 |
| 33.355 |
| 33.876 |
| 35.293 |
| 35.816 |
| 37.164 |
| 37.472 |
| 38.521 |
| 38.909 |
| 39.853 |
| 40.536 |
| 41.402 |
| 44.356 |
| 44.906 |
| 47.58 |

What is claimed is:

1. A method for preparing a compound of Formula 1

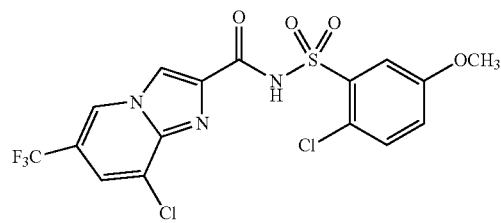

comprising (A) contacting a compound of Formula 2

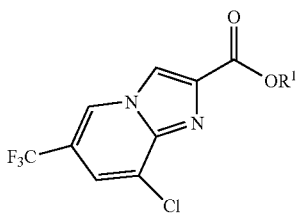

wherein
R¹ is C₁-C₄ alkyl
with a compound of Formula 3

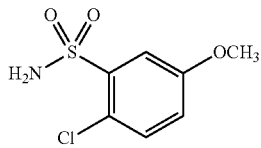

and at least one aluminum reagent of Formula 4

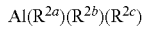

wherein
$R^{2a}$, $R^{2b}$ and $R^{2c}$ are each independently H, Cl or C₁-C₄ alkyl
in the presence of an inert solvent to form a first reaction product,
(B) contacting the first reaction product with an C₁-C₄ alkanol to form a second reaction product
and (C) contacting the second reaction product with water and a protic acid to give the compound of Formula 1.

2. The method of claim 1 wherein R¹ is CH₃ or CH₂CH₃.

3. The method of claim 1 wherein the at least one aluminum reagent of Formula 4 comprises one or more compounds selected from the group consisting of ClAl(CH₂CH₃)₂, Cl₂Al(CH₂CH₃), Al(CH₂CH₃)₃, Al(CH₃)₃, Al[CH₂CH(CH₃)₂]₃ and HAl[CH₂CH(CH₃)₂]₂.

4. The method of claim 3 wherein the at least one aluminum reagent of Formula 4 comprises ClAl(CH₂CH₃)₂.

5. The method of claim 1 wherein the inert solvent comprises one or more solvents selected from the group consisting of C₁-C₆ haloalkanes, halogenated benzenes and C₇-C₁₀ aromatic hydrocarbons.

6. The method of claim 5 wherein the inert solvent comprises one or more solvents selected from the group consisting of toluene, xylenes, ethylbenzene, cumene, 1,2-dichloroethane, dichloromethane, 1,1,1-trichloroethane, chlorobenzene, 1,2-dichlorobenzene and n-chlorobutane.

7. The method of claim 6 wherein the inert solvent comprises toluene.

8. The method of claim 6 wherein the inert solvent comprises one or more solvents selected from the group consisting of 1,2-dichloroethane, dichloromethane and n-chlorobutane.

9. The method of claim 1 wherein in step (A) the temperature is in the range of 20 to 150° C.

10. The method of claim 1 wherein in step (A), the compound of Formula 2 and the compound of Formula 3 are combined in the presence of an inert solvent and then the aluminum reagent of Formula 4 is added.

11. The method of claim 1 wherein in step (B) the C₁-C₄ alkanol comprises one or more alkanols selected from the group consisting of methanol, ethanol, n-propanol, iso-propanol, n-butanol, iso-butanol and sec-butanol.

12. The method of claim 11 wherein in step (B) the C₁-C₄ alkanol comprises iso-propanol.

13. The method of claim 1 wherein in step (B) the temperature is in the range of 20 to 80° C.

14. The method of claim 1 wherein in step (C) the protic acid comprises one or more protic acids selected from the group consisting of acetic acid, hydrochloric acid, citric acid, formic acid and sulfuric acid.

15. The method of claim 14 wherein in step (C) the protic acid comprises acetic acid.

\* \* \* \* \*